United States Patent [19]

Rautakorpi et al.

[11] Patent Number: 4,708,011

[45] Date of Patent: Nov. 24, 1987

[54] APPARATUS AND METHOD FOR DETERMINING THE PROPERTIES OF FIBER PULP

[75] Inventors: Paavo Rautakorpi, Tampere; Risto Mänttäri, Anjala; Heikki Liimatainen, Inkeroinen; Heikki Pernu, Nattari; Heikki Tuomainen; Hannu Rusanen, both of Tampere, all of Finland

[73] Assignee: OY Tampella AB, Tampere, Finland

[21] Appl. No.: 857,473

[22] Filed: Apr. 30, 1986

[30] Foreign Application Priority Data

May 3, 1985 [FI] Finland ................... 851770

[51] Int. Cl.⁴ .............. G01N 5/00; G01N 11/02
[52] U.S. Cl. ..................... 73/63; 73/1 B; 73/61 R; 162/263; 162/49
[58] Field of Search ........... 73/63, 1 R, 1 B, 61 R; 162/49, 263

[56] References Cited

U.S. PATENT DOCUMENTS

| | | |
|---|---|---|
| 2,602,325 | 7/1952 | Campbell et al. ............ 73/63 |
| 3,206,969 | 9/1965 | Irving ........................ 73/63 |
| 3,368,392 | 2/1968 | Miller ........................ 73/63 |

FOREIGN PATENT DOCUMENTS

| | | | |
|---|---|---|---|
| 467092 | 8/1950 | Canada ....................... 73/63 |
| 830534 | 2/1985 | Finland . | |
| 164705 | 10/1964 | U.S.S.R. ..................... 73/63 |
| 718519 | 2/1980 | U.S.S.R. ..................... 73/63 |

Primary Examiner—Tom Noland
Attorney, Agent, or Firm—Roylance, Abrams, Berdo & Goodman

[57] ABSTRACT

The invention relates to an apparatus and method for measuring the properties of fiber pulp. The apparatus used in the method comprises a batching vessel (1) for measuring the volume and temperature of the sample; a filtering chamber (3, 5) by means of which the sample is filtered on a wire (4) by means of a pressure difference, and an air flow is produced through the pulp cake formed during the filtration. The apparatus has, next to the filtering chamber (3, 5), a raisable vertical central shaft (8), which can be rotated in steps, and holders for transferring the wire (4) together with the pulp cake to positions around the central shaft (8) for the functions, and for returning the wire (4) into the filtering chamber.

34 Claims, 2 Drawing Figures

APPARATUS AND METHOD FOR DETERMINING THE PROPERTIES OF FIBER PULP

BACKGROUND OF THE INVENTION

1. Field of the Invention

The present invention relates to an apparatus and method for measuring the properties of fiber pulp, wherein the volume and temperature of a pulp sample are measured, the sample is filtered, by using a pressure difference, in a filtering chamber onto a wire, the air resistance, weight and possibly other properties of the pulp cake thereby formed are measured, the cake is removed from the apparatus, and the devices are washed and calibrated.

2. Description of the Related Art

From Patent Application FI No. 830534 a method and apparatus are known for determining the properties of a fiber pulp of varying consistency without predilut- ing the fiber pulp. According to the method, the water is first filtered out from the fiber suspension by means of a pressure difference in order to form a pulp cake on a wire, and the pressure difference formed across the pulp cake thereby formed and the volume of air flowing through the cake, i.e. the air resistance of the pulp cake, are measured. The consistency of the fiber suspension is determined by measuring the temperature and air resistance of a fiber suspension batch of predetermined volume and by weighing the pulp cake filtered on the wire. According to Patent Application FI No. 830534, the filtration is carried out using either an endless belt wire, in which case the pulp cake is detached by means of an air nozzle (FIG. 1), or a fixed flat wire, in which case the cake is detached by using a scraper (FIG. 2). In both alternatives the pulp cake is detached from the wire and transferred onto scales for weighing, and this has caused problems, especially at the extremes of the consistency range of the pulp suspension.

In the present invention the above problems have been avoided by weighing the pulp cake together with the wire frame, and at the same time one cleaning step has been eliminated. To achieve this, an apparatus and method for determining the properties of fiber pulp by using a transferrable wire frame, completely different from previous ones, have been developed, and the washing and testing steps of the apparatus can also be incorporated into it.

SUMMARY OF THE INVENTION

The essential principle of the invention is that the pulp cake and the wire are weighed together, whereby the problems involved in transferring the pulp cake separately are avoided and, furthermore, the entire pulp cake is with certainty weighed, and no fibers are detached from it and thereby left unweighed. This idea has been implemented by using a separate wire frame in the apparatus; this wire frame can be placed between the upper section and the lower section of the filtering chamber for the duration of the filtering and the measuring of the air resistance, and be then transferred, together with the pulp cake, onto the scales for weighing. After the weighing the wire frame can further be transferred to the washing step, in which the pulp cake, with all its fibers, is washed off the wire. This is done most advantageously by turning the wire frame upside down for the duration of the washing, whereby all the fibers are detached and fall off the wire during the washing.

By using a separate wire frame it is also possible to attend to the calibration of the scales, since the weight of the wire frame is known. In this case the wire frame can be placed, empty, on the scales, and the scales can be set to indicate, for example, zero in this situation. In this case, when the wire frame is brought onto the scales together with the pulp cake the scales will directly indicate the weight of the pulp cake. The scales can be calibrated, for example, after a certain number of weighings have been performed, or at fixed intervals regardless of the number of weighings, or at some other suitable intervals. Of course, it is possible to use in the measuring several wire frames which are in turns in the filtering chamber for filtering of the pulp cake and, respectively, in the weighing and in the washing. In general, however, one wire frame will suffice for normal measuring needs.

The wire frame can be transferred to a position between the upper section and the lower section of the filtering chamber, and from there onto the scales, in several different ways, either by using a simple manipulator, some kind of conveyor, or the like. Depending on the transferring device, suitable gripping means must, of course, be linked to the wire frame.

The wire frame can be used not only as a filtering wire but also as a washing frame for the filtering chamber and as a calibration frame.

In addition to the mere wire frame it is, of course, possible to connect to the apparatus various auxiliary means for the purposes of checking and cleaning of the apparatus. In this case it is possible to use a separate permeability-measuring frame, the permeability to air or permeability to water of which is precisely known. In this case, by placing such a frame between the upper section and the lower section of the filtering chamber, the air suction capacity of the apparatus can be measured, in terms of either an air flow or a liquid flow. In addition, it is possible to use a separate washing frame, by means of which the filtering chamber can be washed in order to ensure measuring precision. By incorporating different measuring and checking frames in this way into the same measuring apparatus, a very versatile and precise measuring apparatus is obtained. The same way as the wire frame can, also the auxiliary frames can be transferred into the filtering chamber and out of it by different methods, and thus what applies to the transfer and handling of the wire frame can also be applied to these auxiliary frames.

One preferred embodiment of the invention is based on a vertical central shaft, located next to the filtering chamber, together with holders by means of which the wire frame together with the pulp cake, and the possible calibration and washing frames, are transferred to the weighing, washing, etc., positions around the shaft. The central shaft, which can be rotated in steps and to which the wire frame and the possible calibration and washing frames are attached, can also be moved in the vertical direction by using a lifting means which preferably at the same time opens to a slight degree the upper and lower sections of the filtering chamber and possibly the washing means, thereby enabling the wire frame and the possible calibration and washing frames to be transferred from one position to another. The wire frame and the above-mentioned frames preferably have each a centering cone releasing them from their holders when they are lowered in place, for example on scales. They can also be advantageously turned upside down by using turning means, for example when on the washing vessel, whereby the removing and washing of the cake are facilitated.

According to another preferred embodiment of the invention, the filtering chamber is opened by a lifting movement focussed on the central shaft. The same movement lifts the wire frame, detaching it from the lower chamber, and centers the wire frame by means of the centering cone. The detached and centered wire frame is transferred onto the scales by rotating the central shaft. Simultaneously the washing frame of the filtering chamber moves to a position between the upper section and the lower section of the chamber. When the central shaft is lowered, the chambers close so that washing can take place, and the wire frame is lowered onto the scales, being released by the centering cone for weighing. After the weighing and the washing of the chamber, by lifting and rotating the central shaft to a third position the wire frame is brought on top of the washing vessel and the calibration frame to a position between the upper section and the lower section of the filtering chamber. By lowering the central shaft it is possible to test the vacuum system by using a calibration plate, and by turning the wire frame upside down by using a turning means on top of the washing vessel the pulp cake can be removed easily and the wire can be washed by using a spray aimed at the wire. The apparatus can be returned to the filtering position by raising and turning the central shaft, whereupon the calibration frame is lowered onto the scales and the scales can be tested. The results obtained by using the apparatus and method according to the present invention can be used advantageously for calculating the properties of the pulp.

By using the system described above, time can be saved by performing several process functions simultaneously, for example filtering and the testing of the scales weighing and the washing of the chamber washing of the wire and the testing of the vacuum by using a solid or a perforated plate.

It is also possible to add other functions, for example the determination of the bursting strength, to the system according to the invention.

BRIEF DESCRIPTION OF THE DRAWINGS

The invention is described below in greater detail with reference to the accompanying drawing, in which.

DESCRIPTION OF THE PREFERRED EMBODIMENTS

Figure 1:
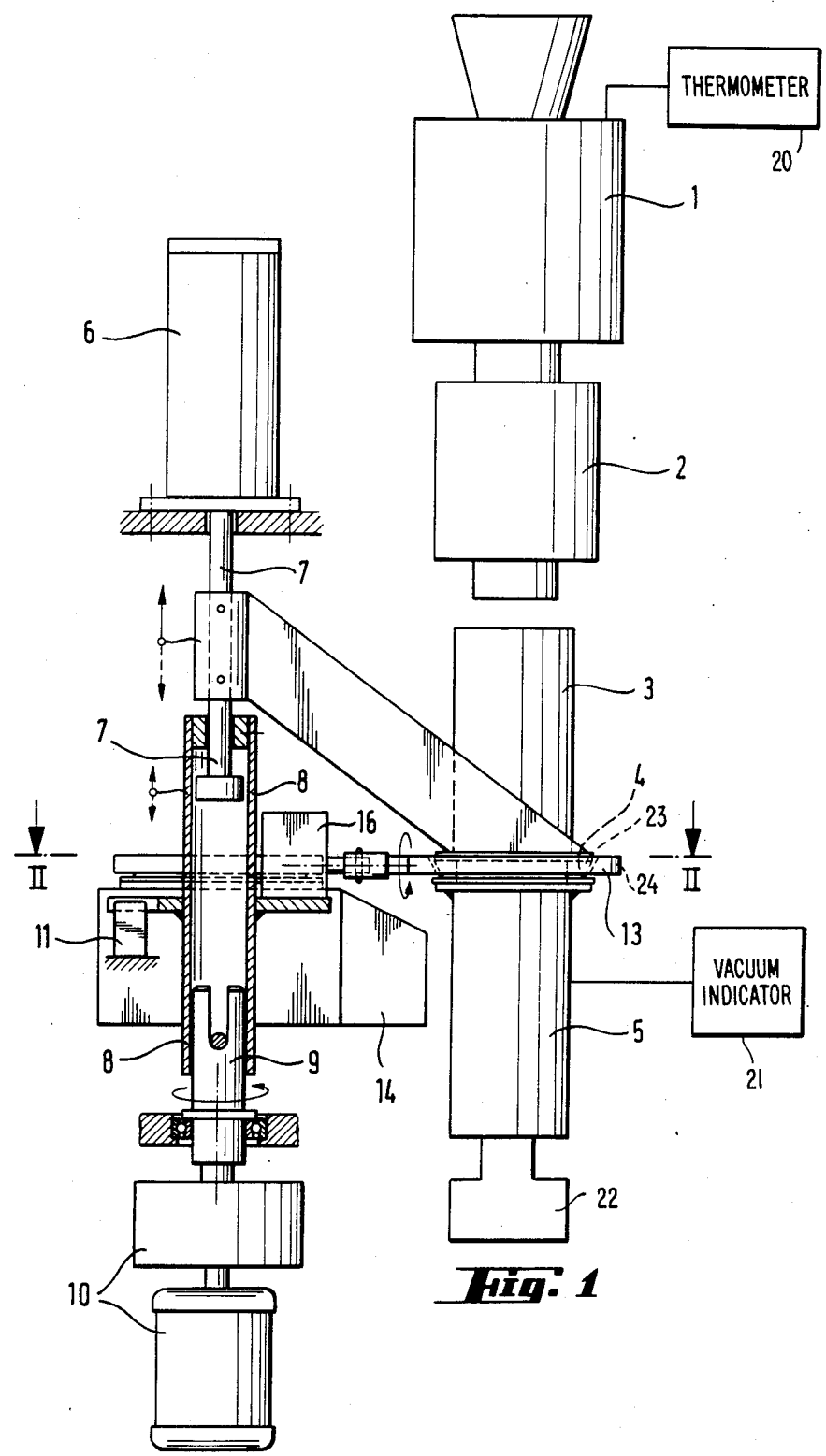
FIG. 1 is a vertical representation of a preferred embodiment of the invention.

According to FIG. 1, the sample to be tested is first introduced into the batching vessel 1 provided with a thermometer 20 and a cooler, and from the vessel 1 the sample, cooled to a certain temperature, is lowered by means of the valve 2 into the upper section, i.e. the filtering mantle 3, of the filtering chamber. The sample is filtered on the wire frame 4 by sucking the water into the vacuum chamber 5. The vacuum is produced by using a vacuum pump 22 and a vacuum vessel. The change in vacuum is measured by vacuum indicator 21 within a certain time interval by sucking air through the filtered sample.

By using lifting means 6 the filtering mantle 3 and, by mediation of shaft 7, the central shaft 8 are lifted in such a way that the central shaft 8 can be rotated to the next position by using the rotating shaft 9 and the rotating means 10. During the lowering the position of the central shaft is ensured by the guide 11.

Figure 2:
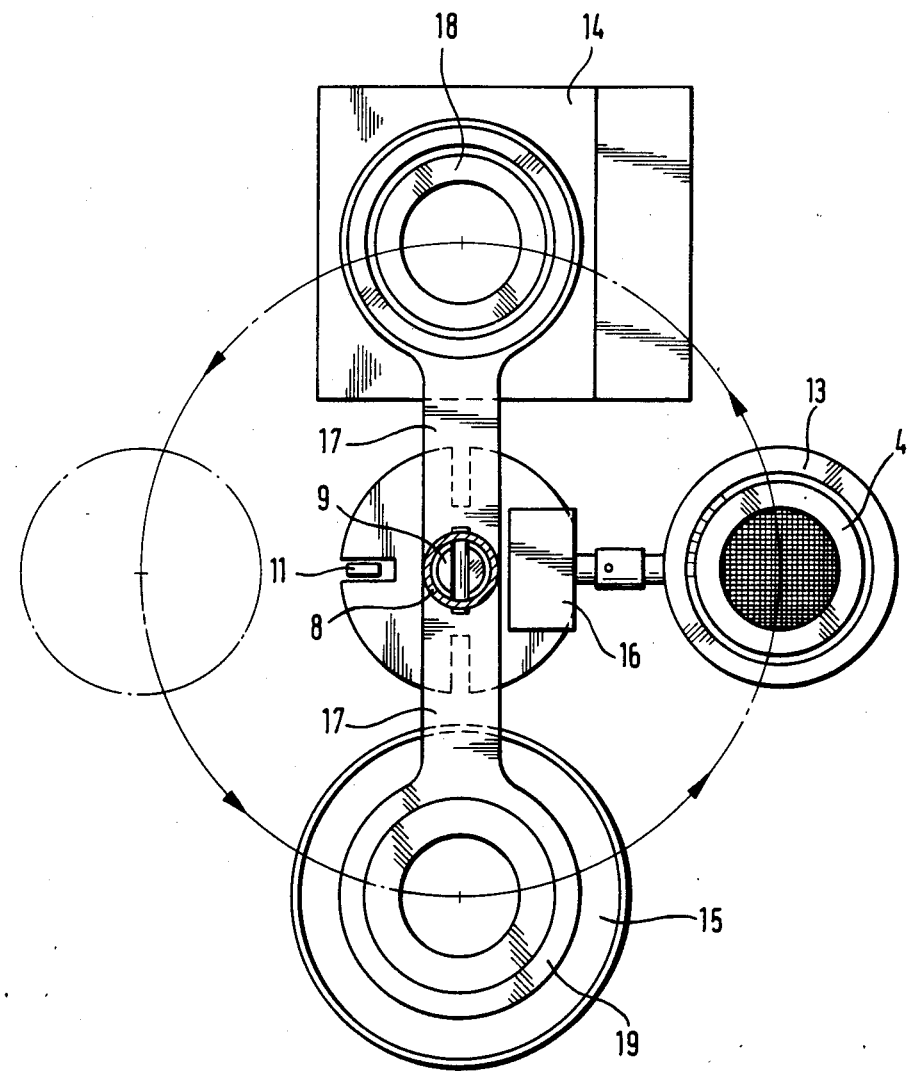
FIG. 2 depicts a top view of the same preferred embodiment of the invention.

In the manner described above the wire frame 4 together with the sample can be transferred by means of the lifting ring 13 onto the scales 14 shown in FIG. 2. When being lowered onto the scales 14, the wire frame 4 is released, so that it can be returned, from the lifting ring 13 by the cone 23 in the wire frame, and the wire frame can be weighed. As seen in FIG. 1, cone 23 is simply an inverted, truncated, conical, radially outwardly extending peripheral surface of wire frame 4. Likewise, cone 24 is an inverted, truncated, conical, radially inwardly extending peripheral surface on lifting ring 13. Respectively, the wire frame 4 together with the sample can be transferred onto the washing vessel 15, be turned upside down by turning means 16, and be washed, for example by spraying it from above.

It is possible to attach to the central shaft, in accordance with FIG. 2, a calibration frame 18 by means of a ring arm 17 for the testing of the scales and the vacuum system, and a washing frame 19 for the washing of the vacuum chamber 5 and the filtering mantle 3. The washing is effected by running water into the vacuum chamber, from where it rises into the overflow pipe of the filtering mantle 3.

We claim:

1. An apparatus for measuring properties of fiber pulp, comprising:
   a batching vessel for conveying a volume of fiber pulp sample;
   a filtering chamber engagable with said batching vessel for receiving said volume of fiber pulp sample therefrom;
   vacuum generating means attached to said filtering chamber for generating a reduced pressure within said chamber for filtering said volume of fiber pulp sample in said filtering chamber;
   a wire frame for filtering said volume of fiber pulp sample in said filtering chamber, said filtering chamber having means for positioning said wire frame therein at a first position for receiving said volume of fiber pulp sample from said batching vessel;
   weighing means for measuring the weight of the filtered sample together with said wire frame, said weighing means being located at a second position spaced from said first position; and
   powered transfer means for moving said wire frame between said first and second positions;
   whereby, after said sample is filtered on said wire frame, said wire frame and said filtered sample are moved by said powered transfer means from said first position to said second position where said wire frame and said filtered sample are weighed.

2. The apparatus of claim 1, further comprising:
   means, attached to said batching vessel, for measuring the temperature of said volume of fiber pulp sample; and
   means, attached to said filtering chamber, for measuring air resistance of said filtered sample.

3. The apparatus of claim 1, further comprising:
   cleaning means for removing said filtered sample from said wire frame, said cleaning means being located at a third position spaced from said first and second positions, and said powered transfer means moving said wire frame between said first, second and third positions.

4. The apparatus of claim 3, wherein:
said powered transfer means includes turning means for inverting the wire frame; and
said cleaning means includes washing means.

5. The apparatus of claim 4, further comprising:
means, attached to said batching vessel, for measuring the temperature of said volume of fiber pulp sample; and
means, attached to said filtering chamber, for measuring the air resistance of said filtered sample.

6. The apparatus of claim 1 wherein said powered transfer means comprises support means and holding means attached to said support means, said holding means releasably couplable to said wire frame.

7. The apparatus of claim 6, wherein:
said support means comprises a shaft positioned substantially equidistant from said first and second positions, said shaft being raisable and rotatable about its central longitudinal axid for transferring said wire frame between said first and second positions by coupling said holding means to said wire frame, rotating said shaft, and uncoupling said wire frame from said holding means.

8. The apparatus of claim 7, wherein the filtering chamber comprises:
a filtering mantle that is couplable to and communicable with said batching vessel; and
a vacuum chamber spaced from said filtering mantle, and attached to said vacuum generating means, said first position being located between said filtering mantle and said vacuum chamber.

9. The apparatus of claim 8, wherein said holding means comprises:
a first arm extending substantially radially outwardly from said shaft; and
a lifting ring attached to said first arm for releasably engaging and lifting said wire frame.

10. The apparatus of claim 9, further comprising:
a central axle having its longitudinal axis substantially coaxially aligned with said central longitudinal axis of said shaft, said axle being reciprocable within a substantially longitudinal bore in said shaft;
lifting means attached to said axle for raising and lowering said axle;
a second arm connecting said axle to said filtering mantle; and
stopping means, attached to said axle, for limiting axle reciprocation independent of shaft reciprocation, said stopping means comprising
a first projection extending radially outwardly from said axle, and
a second projection extending radially inwardly from said shaft, such that when said axle, and correspondingly said mantle, are raised a predetermined leeway, said first projection engages said second projection, and further raising of said axle causes said shaft to rise.

11. The apparatus of claim 10, wherein:
said axle is sufficiently long such that a first section of said axle extends out of a first end of said bore during all reciprocating movement;
said lifting means is located outside of said shaft and is coupled to said first section of said axle;
said second arm is attached to said first section of said axle;
said first projection is located on a second section of said axle reciprocating entirely within said bore; and
said second projection is located in said bore.

12. The apparatus of claim 11, wherein said wire frame has a radially outwardly facing peripheral edge that decreases in diameter from the top of said edge to the bottom of said edge.

13. The apparatus of claim 12, wherein:
said edge has the shape of an inverted truncated cone; and
said lifting ring has a radially inwardly facing peripheral edge having the shape of an inverted truncated cone such that said radially outwardly facing edge of said wire frame is positionable within said radially inwardly facing edge of said lifting ring, and when said lifting ring is raised, said radially inwardly facing edge engages said radially outwardly facing edge, thereby releasably coupling said lifting ring to said wire frame.

14. The apparatus of claim 13, further comprising:
means, attached to said batching vessel, for measuring the temperature of said volume of fiber pulp sample; and
means, attached to said filtering chamber, for measuring the air resistance of said filtered sample.

15. The apparatus of claim 10, further comprising:
cleaning means for removing said filtered sample from said wire frame, said cleaning means being located at a third position spaced from said first and second positions, and said powered transfer means moving said wire frame between said first, second and third positions.

16. The apparatus of claim 15, wherein:
said powered transfer means includes turning means for inverting the wire frame; and
said cleaning means includes washing means.

17. The apparatus of claim 16, further comprising:
means, attached to said batching vessel, for measuring the temperature of said volume of fiber pulp sample; and
means, attached to said vacuum chamber, for measuring the air resistance of said filtered sample.

18. The apparatus of claim 17, further comprising:
at least one additional arm extending outwardly from said shaft, said additional arm having an additional lifting ring attached thereto for engaging and lifting an additional wire frame.

19. The apparatus of claim 18, wherein:
said axle is sufficiently long such that a first section of said axle extends out of a first end of said bore during all reciprocating movement;
said lifting means is located outside of said shaft and is coupled to said first section of said axle;
said second arm is attached to said first section of said axle;
said first projection is located on a second section of said axle reciprocating entirely within said bore; and
said second projection is located in said bore.

20. The apparatus of claim 19, wherein each of said wire frames has a radially outwardly facing peripheral edge that decreases in diameter from the top of said edge to the bottom of said edge.

21. The apparatus of claim 20, wherein:
said edge has the shape of an inverted truncated cone; and said lifting ring has a radially inwardly facing peripheral edge having the shape of an inverted truncated cone such that said radially outwardly facing edge of said wire frame is positionable within said radially inwardly facing edge of said lifting ring, and when said lifting ring is raised, said radially inwardly facing edge engages said radially outwardly facing edge, thereby releasably coupling said lifting ring to said wire frame.

22. The apparatus of claim 15, wherein said first, second and third stations are substantially coplanar.

23. A method for measuring properties of a sample of fiber pulp, comprising the steps of:
determining the volume and temperature of the sample using volume and temperature measurement means,
conveying the sample to a filtering chamber,
filtering the sample on a separate wire frame under a pressure differential,
measuring the air resistance of the filtered sample,
transferring the wire frame and filtered sample, by powered means, to weighing means for measuring the combined weight of the wire frame and filtered sample, and
weighing the wire frame and filtered sample.

24. The method of claim 23, further comprising, after the weighing step, the steps of
transferring the wire frame and filtered sample to a sample removal area, and
removing the filtered sample from the wire frame.

25. The method of claim 24, wherein said removing step is carried out by washing said wire frame.

26. The method of claim 25, wherein, using turning means, the wire frame is inverted and positioned onto a washing vessel to facilitate removing the filtered sample from the wire frame.

27. The method of claim 24, wherein
the steps of filtering, weighing and removing are carried out at separate positions located spatially apart from each other,
the transferring steps are carried out using a substantially vertical, raisable, rotatable, central shaft positioned substantially equidistant from each of the positions, the shaft having at least a first arm extending substantially radially outwardly from the shaft, the first arm having a lifting ring attached thereto, which ring can releasably couple to the wire frame, and
raising or rotating the shaft can raise or rotate the lifting ring and releasably coupled wire frame.

28. The method of claim 27, wherein
the filtering chamber is comprised of a vacuum chamber connected to a vacuum generator, and a filtering mantle spatially separated from the vacuum chamber, and
the step of filtering is carried out by
collecting the sample in the filtering mantle,
passing the sample onto the wire frame,
removing, by means of the vacuum chamber, water from the sample, through the wire frame, and into the vacuum chamber.

29. The method of claim 28, wherein the step of measuring the air resistance is carried out by
drawing air through the filtered sample by means of the vacuum chamber, and
recording the pressure difference and air flow.

30. The method of claim 28, wherein the filtering mantle is attached to an axle reciprocating partially within, and coaxially along a bore located substantially along the longitudinal axis of the shaft, the axle being provided with a length of leeway over which the axle and, correspondingly, the mantle can be reciprocatingly raised and lowered without raising the shaft, and
the step of transferring the wire frame and filtered sample from the vacuum chamber to the weighing means comprises
raising the axle for the length of the leeway, thereby raising the mantle,
further raising the axle, thereby also raising the shaft, and
rotating the shaft.

31. The method of claim 27, wherein at least one of the steps of transferring comprises
releasably coupling the lifting ring to the wire frame,
raising the shaft and, correspondingly, the lifting ring releasably coupled to the wire frame, and
rotating the shaft, thereby rotating the lifting ring and wire frame.

32. The method of claim 31, wherein
the wire frame has a radially outwardly facing peripheral edge having the shape of an inverted truncated cone, and the lifting ring has a radially inwardly facing peripheral edge having the shape of an inverted truncated cone, the radially outwardly facing edge of the wire frame being positionable within the radially inwardly facing edge of the lifting ring, such that when the lifting ring is raised, the radially inwardly facing edge engages the radially outwardly facing edge, thereby releasably coupling the lifting ring to the wire frame, and
the step of weighing is carried out by
positioning the lifting ring and releasably coupled wire frame above the weighing means by rotating the shaft,
lowering the lifting ring and wire frame onto the weighing means until the wire frame is supported by the weighing means, and
further lowering the lifting ring until the peripheral edge of the lifting ring disengages the peripheral edge of the wire frame, hereby releasing the wire frame onto the weighing means.

33. The method of claim 27, further comprising, prior to the step of weighing the wire frame and filtered sample, the step of
calibrating the weighing means using a calibration frame releasably coupled to another lifting ring, the ring being connected to the shaft by another substantially radially outwardly extending arm.

34. The method of claim 27, further comprising, after the step of transferring the wire frame and filtered sample from the vacuum chamber to the weighing means, the step of
washing the filtering chamber using a washing frame releasably coupled to another lifting ring, the ring being connected to the shaft by another substantially radially outwardly extending arm.

* * * * *